(12) United States Patent
Muhanna (10) Patent No.: US 8,182,512 B2
(45) Date of Patent: May 22, 2012

(54) FACET JOINT PROSTHETIC REPLACEMENT AND METHOD

(76) Inventor: Nabil L. Muhanna, Gainesville, GA (US)

( * ) Notice: Subject to any disclaimer, the term of this patent is extended or adjusted under 35 U.S.C. 154(b) by 205 days.

(21) Appl. No.: 12/704,096

(22) Filed: Feb. 11, 2010

(65) Prior Publication Data

US 2010/0211107 A1 Aug. 19, 2010

Related U.S. Application Data

(60) Provisional application No. 61/152,279, filed on Feb. 13, 2009.

(51) Int. Cl.
*A61B 17/70* (2006.01)
(52) U.S. Cl. .......... 606/247; 606/256; 606/257
(58) Field of Classification Search .......... 606/246–279; 403/122, 124, 131
See application file for complete search history.

(56) References Cited

U.S. PATENT DOCUMENTS

| | | | |
|---|---|---|---|
| 3,867,728 A | 2/1975 | Studstad et al. | |
| 5,540,688 A * | 7/1996 | Navas | 606/266 |
| 6,241,730 B1 * | 6/2001 | Alby | 606/256 |
| 6,296,644 B1 * | 10/2001 | Saurat et al. | 606/256 |
| 7,686,833 B1 * | 3/2010 | Muhanna et al. | 606/257 |
| 7,862,586 B2 * | 1/2011 | Malek | 606/246 |
| 8,007,519 B2 * | 8/2011 | Hudgins et al. | 606/255 |
| 8,029,545 B2 * | 10/2011 | Graf et al. | 606/256 |
| 2004/0260287 A1 | 12/2004 | Ferree | |
| 2005/0055096 A1 | 3/2005 | Serhan et al. | |
| 2005/0113927 A1 * | 5/2005 | Malek | 623/17.16 |
| 2005/0267472 A1 * | 12/2005 | Biedermann et al. | 606/61 |
| 2006/0200136 A1 * | 9/2006 | Jackson | 606/61 |
| 2006/0229609 A1 * | 10/2006 | Wang | 606/61 |
| 2008/0234744 A1 * | 9/2008 | Zylber et al. | 606/264 |
| 2009/0069849 A1 * | 3/2009 | Oh et al. | 606/246 |

OTHER PUBLICATIONS

Office Action dated Oct. 28, 2011, for related U.S. Appl. No. 12/240,182, filed Sep. 29, 2008.

* cited by examiner

*Primary Examiner* — Eduardo C Robert
*Assistant Examiner* — Jan Christopher Merene
(74) *Attorney, Agent, or Firm* — Womble Carlyle Sandridge & Rice, LLP (57) ABSTRACT

The present disclosure provides prosthesis, methods, and kits for replacing a facet joint, in particular prosthesis, methods, and kits for replacing a spinal motion segment comprising a facet joint. The prosthesis includes a first and second member that interlock to form a sliding joint.

6 Claims, 3 Drawing Sheets

FACET JOINT PROSTHETIC REPLACEMENT AND METHOD

CROSS REFERENCE TO RELATED APPLICATION

This application claims the benefit of U.S. provisional patent application No. 61/152,279, filed Feb. 13, 2009.

FIELD OF THE DISCLOSURE

The present disclosure relates to prosthesis, methods, and kits for replacing a facet joint and, in particular, for replacing a spinal motion segment comprising a facet joint.

BACKGROUND

The spinal column, which is the central support to the vertebrate skeleton and a protective enclosure for the spinal cord, is a linear series of bones, or vertebrae. Intervertebral discs separate and reduce friction between adjacent vertebrae and absorb compression forces applied to the spinal column. Spinal nerves that extend from each side of the spinal cord exit the column at intervertebral foramina.

A typical vertebra comprises an anterior body, and a posterior arch that surrounds the spinal cord lying within the vertebral foramen formed by the arch. The muscles that flex the spine are attached to three processes extending from the posterior arch. On the upper surface of each vertebra in a standing human are two superior articulated processes that oppose two inferior articulated processes extending from the lower surface of an adjacent vertebra. Facets on the opposing processes determine the range and direction of movement between adjacent vertebrae, and hence the flexibility of the spinal column.

Back pain is one of the most significant problems facing the workforce in the United States today. It is a leading cause of sickness-related absenteeism and is the main cause of disability for people between ages 19 and 45. Although acute back pain is common and typically treated with analgesics, chronic pain may demand surgery for effective treatment. One of the most common causes of back pain stems from trauma to an intervertebral disc, resulting from mechanical shock, stress, tumors or degenerative disease, which may impair functioning of the disc and limit spinal mobility. In many cases, the disc is permanently damaged and the preferred treatment becomes partial or total excision. Another cause of back injury is herniation of the intervertebral disc, wherein the gelatinous fluid of the nucleus pulposus enters the vertebral canal and pressures the spinal cord. Again, surgery is often the only method available for permanent relief from pain or the neurological damage ensuing from the pressure of fluid on the spinal cord, and requires replacement of the damaged disc.

Traumatic injury to an intervertebral disc that is not removed will frequently promote scar tissue formation. Scar tissue is weaker than original healthy tissue so that the disc will progressively degenerate, lose water content, stiffen and become less effective as a shock absorber. Eventually, the disc may deform, herniate, or collapse, limiting flexibility of the spinal column at that position. The only option is for the intervertebral disc to be partially or totally removed.

Surgical procedures for replacing intervertebral disc material, rather than fusing of the vertebrae, have included both anterior approaches and posterior approaches to the spinal column. The posterior approach (from the back of the patient) encounters the spinous process, superior articular process, and the inferior articular process that must be removed to allow insertion of the disc replacement material into the intervertebral space. The anterior approach to the spinal column is complicated by the internal organs that must be bypassed or circumvented to access the vertebrae.

Degenerative changes of the adult spine have traditionally been determined to be the result of the interrelationship of the intervertebral disc and the facet joints. Degenerative changes in the disc can lead to arthritic changes in the facet joint and vice versa. Although the use of an intervertebral disc prosthesis may achieve some level of success with patients, disc replacement does not address spine pathologies such as spondylolisthesis and spinal stenosis caused by facet joint degeneration or disease It would therefore be an improvement in the art to provide an intervertebral disc prosthesis and/or a facet joint prosthesis and method that replaces the natural disc and/or facet joint so as to remove the source of arthritic, traumatic, or other disease mediated pain.

SUMMARY

In one aspect, the present disclosure provides a facet joint prosthesis for replacing a facet joint. The facet joint prosthesis comprises:

a) a first and a second pedicle screw, wherein each pedicle screw has a screw head; and b) an inner member having an elongated bulbous portion that tapers to a shaft via a neck portion, a centered eyelet having a beveled inner rim that receives and supports the pedicle screw head, the centered eyelet arranged at a distal end of the shaft; and c) an outer member having an open ended elongated bulbous portion that tapers to a shaft via a neck portion, a centered eyelet having a beveled inner rim that receives and supports the pedicle screw head, the centered eyelet arranged at a distal end of the shaft, wherein the open ended elongated bulbous portion has a bulbous shaped cavity and receives the elongated bulbous portion through a cavity slot and the neck portion of the inner portion contacts a cavity wall near an open end of the open ended bulbous portion.

In another embodiment, the facet joint prosthesis further comprises a first, a second, and a third threaded screw. The facet joint assembly comprises:

a) a first, second, and third pedicle screw, wherein each pedicle screw has a screw head;

b) a first inner member having an elongated bulbous portion that tapers to a shaft via a neck portion, a centered eyelet having a beveled inner rim that receives and supports the pedicle screw head, the centered eyelet arranged at a distal end of the shaft;

c) a first outer member having an open ended elongated bulbous portion that tapers to a shaft via a neck portion, an offset eyelet having a beveled inner rim that receives and supports the pedicle screw head, the offset eyelet arranged at a distal end of the shaft and offset in a first direction, wherein the open ended elongated bulbous portion has a bulbous shaped cavity and receives the elongated bulbous portion of the first inner member through a cavity slot and the neck portion of the inner portion contacts a cavity wall near an open end of the open ended bulbous portion;

d) a second inner member having an elongated bulbous portion that tapers to a shaft via a neck portion, an offset eyelet having a beveled inner rim that receives and supports the pedicle screw head and offset in a second direction, the offset eyelet arranged at a distal end of the shaft; and e) a second outer member having an open ended elongated bulbous portion that tapers to a shaft via a neck portion, a centered eyelet having a beveled inner rim that receives and supports the pedicle screw head, the centered eyelet arranged at a distal end of the shaft, wherein the open ended elongated bulbous portion has a bulbous shaped cavity and receives the elongated bulbous portion of the first inner member through a to cavity slot and the neck portion of the inner portion contacts a cavity wall near an open end of the open ended bulbous portion.

In yet another aspect, the present disclosure provides a method for replacing a facet joint of a subject in need of such replacement. The method comprises providing a facet joint prosthesis to the subject, wherein the facet joint prosthesis comprises:

a) providing a first and a second pedicle screw, wherein each pedicle screw has a screw head; and b) providing an inner member having an elongated bulbous portion that tapers to a shaft via a neck portion, a centered eyelet having a beveled inner rim that receives and supports the pedicle screw head, the centered eyelet arranged a distal end of the shaft; and c) providing an outer member having an open ended elongated bulbous portion that tapers to a shaft via a neck portion, a centered eyelet having a beveled inner rim that receives and supports the pedicle screw head, the centered eyelet arranged a distal end of the shaft, wherein the open ended elongated bulbous portion has a bulbous shaped cavity and receives the elongated bulbous portion through a cavity slot and the neck portion of the inner portion contacts a cavity wall near an open end of the open ended bulbous portion.

In yet another aspect, the present disclosure provides a kit for replacing a facet joint of a subject in need of such replacement. The kit comprises a facet joint prosthesis to the subject, wherein the facet joint prosthesis comprises:

a) a first, second, and third pedicle screw, wherein each pedicle screw has a screw head;

b) a first inner member having an elongated bulbous portion that tapers to a shaft via a neck portion, a centered eyelet having a beveled inner rim that receives and supports the pedicle screw head, the centered eyelet arranged at a distal end of the shaft;

c) a first outer member having an open ended elongated bulbous portion that tapers to a shaft via a neck portion, an offset eyelet having a beveled inner rim that receives and supports the pedicle screw head, the offset eyelet arranged at a distal end of the shaft and offset in a first direction, wherein the open ended elongated bulbous portion has a bulbous shaped cavity and receives the elongated bulbous portion of the first inner member through a cavity slot and the neck portion of the inner portion contacts a cavity wall near an open end of the open ended bulbous portion;

d) a second inner member having an elongated bulbous portion that tapers to a shaft via a neck portion, an offset eyelet having a beveled inner rim that receives and supports the pedicle screw head and offset in a second direction, the offset eyelet arranged at a distal end of the shaft;

e) a second outer member having an open ended elongated bulbous portion that tapers to a shaft via a neck portion, a centered eyelet having a beveled inner rim that receives and supports the pedicle screw head, the centered eyelet arranged at a distal end of the shaft, wherein the open ended elongated bulbous portion has a bulbous shaped cavity and receives the elongated bulbous portion of the first inner member through a cavity slot and the neck portion of the inner portion contacts a cavity wall near an open end of the open ended bulbous portion;

f) a disk replacement element;

g) assembly and installation harware.

In still yet another aspect, the present disclosure provides a facet joint prosthesis for replacing a facet joint. The facet joint prosthesis comprises:

a) a first and a second pedicle screw, wherein the first and second pedicle screw each comprise a threaded shaft and a screw head;

b) an outer member comprising a first end and a second end, wherein the first end comprises an open ended elongate bulbous portion, the open ended elongate bulbous portion having an open end and an elongate bulbous cavity central to the elongate bulbous portion, the elongate bulbous portion tapers to a shaft via a neck portion, the shaft extending toward the second end, wherein the second end comprises an eyelet having a central passage that receives the first pedicle screw and a beveled inner rim that surrounds the central passage and supports the first pedicle screw head; and c) an inner member comprising a first end and a second end, wherein the first end comprises an elongate bulbous portion that tapers to a shaft via a neck portion, the shaft extending toward the second end, wherein the second end comprises an eyelet having a central passage that receives the second pedicle screw and a beveled inner rim that surrounds the central passage and supports the second pedicle screw head, wherein the elongate bulbous cavity of the outer member receives the elongate bulbous portion of the inner member through a cavity slot in the open ended elongate bulbous portion of the outer member, the neck portion of the inner member contacting a cavity wall near the open end of the open ended elongate bulbous portion of the outer member, the elongate bulbous portion of the outer member and the elongate bulbous cavity and the elongate bulbous portion of the outer member being elongated in a longitudinal direction.

BRIEF DESCRIPTION OF THE DRAWINGS

The present disclosure is now described with respect to the embodiments seen in following drawings. According to common practice, the various features of the drawings discussed below are not necessarily drawn to scale. Dimensions of various features and elements in the drawings may be expanded or reduced to illustrate more clearly the embodiments of the disclosure.

DETAILED DESCRIPTION OF THE DISCLOSURE

Referring generally to the figures, there is shown an assembly, and individual components, for a facet joint prosthesis. In general, the facet joint prosthesis is comprised of an inner member having a bulbous portion linked to a bulbous cavity of an outer member. The facet joint prosthesis assembly is anchored to a patient's spine by a plurality of pedicle screws inserted through eyelets that are integral to the inner and outer members.

The terms "articulate," "articulation," or "articulating," as used herein, refer broadly to rotational movement and linear movement involving any combination of pitch, roll, yaw, and translational motion. Generally, rotational motion is the spinning of an object about any one of the three Cartesian axes. The three linear degrees of freedom are described in common language terms such as forward/backward, up/down, and side/side. These linear directions can also be used to define axes of rotation for rotational motion as well as axes of translational movement. Rotation about the forward/backward axis can be called roll, rotation about the up/down axis can be called yaw, and rotation about the side/side axis can be called pitch.

The below listed components, which are mentioned throughout this specification, are identified in the drawings by the reference numeral juxtaposed below:

Facet Joint Prosthesis—10
First Inner Member—12a
Second Inner Member—12b
Shaft of Inner Member—13
Elongated Bulbous Feature/Portion of Inner Member—14
Attachment Feature/Eyelet—15a
Attachment Feature/Offset Eyelet—15b
Neck Region of Inner Member—16
Facets of Inner Member—17
First Outer Member—20a
Second Outer Member—20b
Shaft of Outer Member—21
Elongated Bulbous Portion of Outer Member—22
Cavity in Outer Member—23
Inner Wall of Cavity—24
Open End of Cavity/Outer Member—25
Cavity Slot/Channel—26
Neck Region of Outer Member—27
Beveled, Centrally Located Chamber—30
Pedicle Screws—32
Threaded Insertion Portion of Pedicle Screw—33
Screwhead of Pedicle Screw—34

Figures 1, 2:
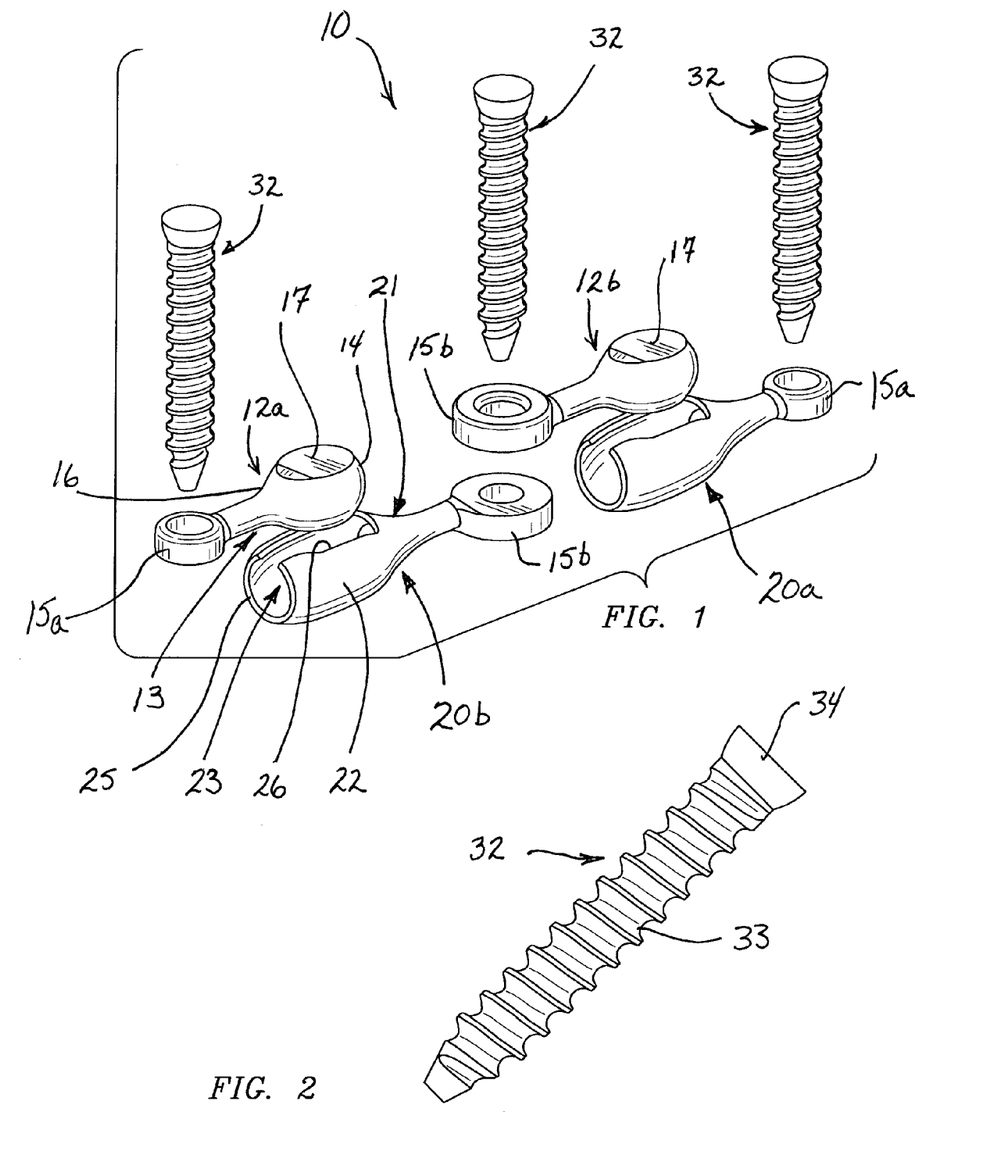
FIG. 1 is an illustration of an exploded view of one embodiment of a facet joint prosthesis in accordance with the present disclosure.
FIG. 2 is an illustration of a pedicle screw in accordance with the present disclosure.

Referring now in more detail to the drawings, FIG. 1 illustrates a present embodiment of the disclosure in a preferred form. Generally, disclosed is a facet joint that is used as a replacement joint fitting within an intervertebral space (not shown). The elements of the facet joint include at least one inner member that are received in an interlocking fashion by an outer member, each member having a screw, or anchoring feature, to affix the inner member and the outer member to their respective vertebrae. Although the replacement facet joint illustrated in FIG. 1 has a plurality of inner and outer members that are linked together forming a facet joint capable of spanning the space between multiple vertebrae, it will be understood by the skilled artisan that the most basic facet joint can be assembled from a single inner member and its screw, and a single outer member and its screw. The inner member is illustrated as a shaft having an elongated, bulbous feature on one end, tapering to the shaft having an eyelet, or attachment feature, arranged on the other end. The elongated, bulbous feature is sized and configured to fit within a cavity of the outer member. The inner member is illustrated as a shaft having an elongated, bulbous feature on one end, tapering to the shaft having an eyelet, or attachment feature, arranged on the other end. The cavity of the outer member is arranged within the elongated, bulbous feature and is accessed by a slot extending from the outer surface of the elongated, bulbous feature to the cavity. The shape of a cavity inner wall, which defines the boundary of the cavity, is approximately that of an outer surface of the elongated, bulbous feature of the inner member. The inner member and outer member fit together to form an interconnected link capable of movement through a wide range of motion and at a minimum motion of a twisting, a rotating, a sliding fashion, and combinations thereof.

FIG. 2 illustrates a pedicle screw in accordance with the present disclosure and in a preferred form. The pedicle screw has a longitudinal axis along which a threaded insertion portion is aligned. At one end of the threaded insertion portion of the pedicle screw is located a screw head. The screw head expands from a base to the top of the screw head, wherein a feature may be located to aid or facilitate twisting the screw to insert. For example, an upper surface of the screw is provided with a socket configured to receive an "Allen-type" hexwrench, or the like, for screwing and unscrewing the clamping screw. The profile of the expanding portion of the screw head is preferably that of a conic section (i.e. a parabolic, spherical, conical, hyperbolic, or elliptical). However, it is not required that the profile be a conic section and other profiles, such as a linear profile, would be acceptable depending on the application and requirements. The pedicle screw typically has a diameter of 6.5 mm and length sufficient to anchor the system to bone, however other diameters and lengths are acceptable. The screw head has approximately the same diameter of the screw head at the screw/screw head interface and expands to a larger diameter at the top of the screw head. This feature assists with securing a centered eyelet (see FIGS. 1, 5, and 6) to the screw while at the same time permitting relative motion between the screw head and eyelet.

In one embodiment, the pedicle screw is formed of a metal. In another embodiment, the pedicle screw is formed of titanium, or an alloy thereof. In other embodiments, the pedicle screw is formed of a metal that encourages bone growth from a pedicle into the screw member.

Figures 3, 4, 5, 6:
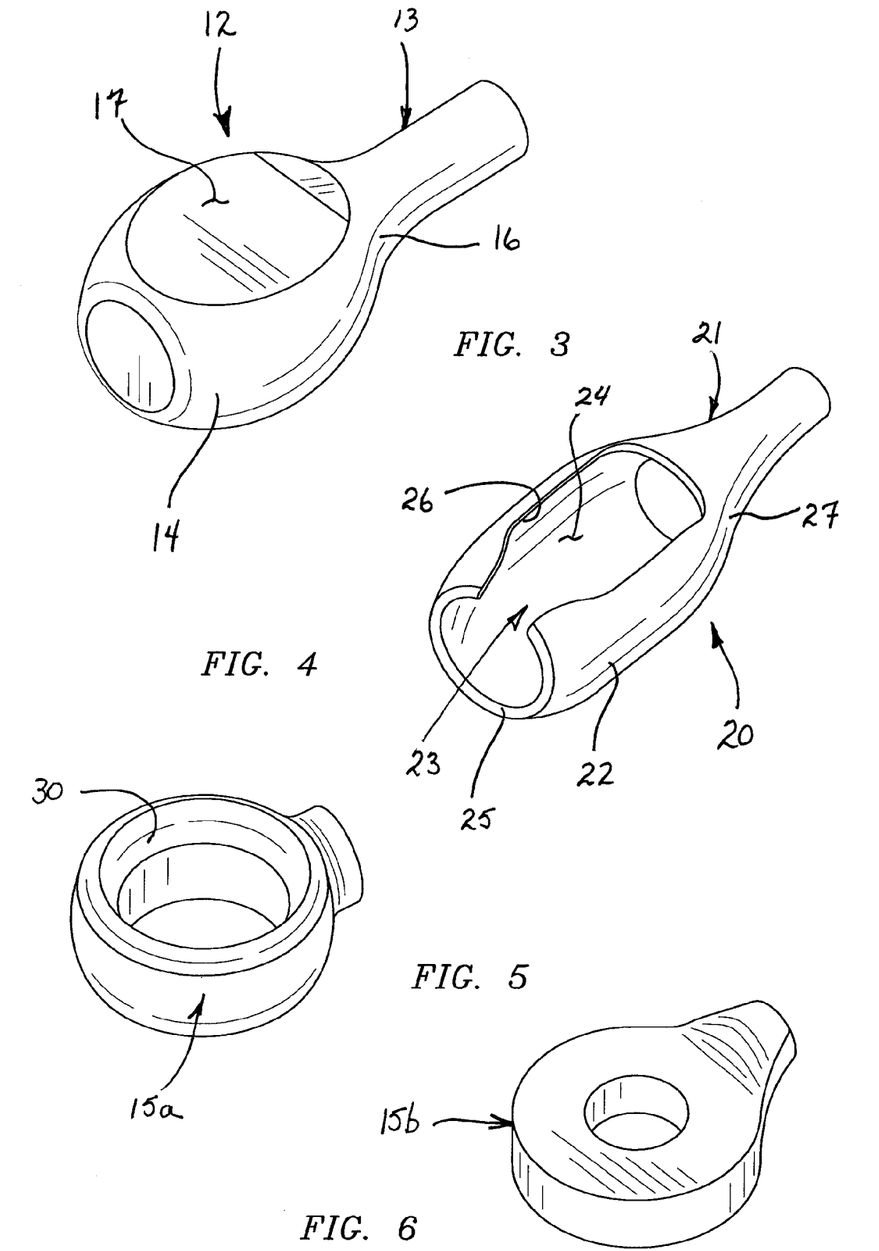
FIG. 3 is an illustration of a perspective view of an inner member in accordance with the present disclosure.
FIG. 4 is an illustration of a perspective view of an outer member in accordance with the present disclosure.
FIG. 5 is an illustration of a perspective view of a centered eyelet in accordance with the present disclosure.
FIG. 6 is an illustration of a perspective view of an offset eyelet in accordance with the present disclosure.

FIG. 3 is an illustration of an inner member of the facet joint prosthetic assembly. The inner member comprises a shaft, having a longitudinal axis, and expands to an elongated bulbous portion via a neck region. A distal end of the shaft includes an attachment feature and the attachment features are illustrated in FIGS. 4 and 5. Although the attachment feature, or eyelet, of FIG. 5 or 6 is not shown attached to the distal end, the inner member is fabricated including the eyelet as a single, monolithic component. The elongated bulbous portion terminates at a flat end that truncates the elongated bulbous portion. In the preferred embodiment, the elongated bulbous portion is ellipsoidal in shape. The shape is not arbitrary, but is such to interface and be in sliding contact with other components in the facet joint prosthesis assembly while enhancing relative motion between the inner member and an outer member (not shown). However, as will be recognized by those skilled in the art, other geometries are acceptable such as spheroids or other obloids. As illustrated, the elongated bulbous portion further comprises a facet. The facet is a flat surface either produced by removing material from the elongated bulbous portion or casting the feature in. The facet may be produced by an appropriate machining operation, cast in, or formed directly into the elongated bulbous portion of the inner member. Furthermore, there may be multiple facets arranged on the periphery of the elongated bulbous portion and in the preferred embodiment, two facets are arranged on opposite sides of the elongated bulbous portion, approximately 180 degrees apart. The facets facilitate installation of the inner member in the assembly by enhancing the ability to insert the elongated bulbous portion of the inner member through a slot, or channel, in the outer member (see FIG. 4). Additionally, there is the advantage of less material being required to manufacture the component and the introduction of less foreign material into a patient. The neck region is shaped to provide a continuous and smooth transition between the shaft and the elongated bulbous portion, matching a contour of the elongated bulbous portion where the neck region intersects or merges and tapering to the shaft. The shaft is sized appropriately to adequately function with the mechanical loading that will be applied to the system during use.

With continued reference to FIG. 3, the inner member is formed from a metal, preferable the same or a similar metal to the pedicle screw. Alternatively, the inner member may be formed of titanium, an alloy thereof, or any alloy benign to the patient's body. As an alternative, the inner member may be formed from a composite or polymer material having demonstrated sufficient mechanical properties for the desired application. Typically, the inner member is sized and configured such that when assembled as an element of the facet joint will provide a facet joint sufficient to span the gap between adjacent vertebrae.

The facet assembly also comprises an outer member, as illustrated in FIG. 4. Similar to the inner member, the outer member also comprises a shaft having a longitudinal axis, a neck region that expands, or flares outwardly, to an elongated bulbous portion that terminates in an open end. The elongated bulbous portion is hollow and comprises a cavity having an inner wall. The cavity is sized and configured to accommodate and receive the elongated bulbous portion of the inner member. The cavity has generally the same shape as elongated bulbous portion of the inner member but is slightly larger in size to allow relative motion between the two components. The cavity decreases in size as the cavity approaches the open end and has approximately the same contour as the neck region of the inner member. A distal end of the shaft includes an attachment feature and the attachment features are illustrated in FIGS. 5 and 6. Although the attachment feature, or eyelet, of FIG. 5 or 6 is not shown attached to the distal end, the outer member is fabricated including the eyelet as a single, monolithic component. When assembled, the inner member and outer member fit together to contact and form a sliding joint. A slot or channel is located in the elongated bulbous region and extends to the open end of the outer member. The slot comprises a rectangular portion and begins to decrease in width via a narrowing portion as it approaches the open end and is at its narrowest at the open end. The skilled artisan will recognize that the slot can be any size or shape necessary to insert the bulbous portion of the inner member into the cavity of the outer member. A portion of the inner wall towards the open end has a contour similar to the contour of elongated bulbous portion, such that when installed, a portion of the neck and elongated bulbous portion of the inner member will be in sliding contact with a portion of the inner wall. The open end is preferably circular and has a diameter larger than the diameter of the shaft of the inner member. This allows for a greater range of motion between the inner member and outer member when assembled.

The outer member may also be formed from a metal, preferable the same or a similar metal to the pedicle screw and the inner member. Similarly, the outer member may be formed of titanium, an alloy thereof, or any alloy benign to the patient's body. As an alternative, the inner member may be formed from a composite or polymer material having demonstrated sufficient mechanical properties for the desired application.

FIGS. 5 and 6 illustrate at least two different types of attachment features, or eyelets, that may be used with the present embodiment. Either the eyelet of FIG. 5 or FIG. 6 may be used with either the inner or outer member and as discussed above, is fabricated to be integral with the inner member or outer member. Generally, only one eyelet will be required for a given inner member or outer member. Referring now to FIG. 5, the eyelet is generally cylindrical in shape with a centrally located opening to accommodate a pedicle screw. The eyelet has an upper surface and a lower surface, with the upper surface being beveled or chamfered at the centrally located chamfer. The lower surface may be chamfered as well at the central opening, but it is not required. The chamfer is sized to match the expansion of the pedicle screw head which, when assembled, would rest within the chamfer of the eyelet. Thus, the contour of the chamfer, rather linear or nonlinear, is meant to approximately match the contour of the pedicle screw head. The thickness of the eyelet is approximately the thickness, or diameter, of the shaft of either the inner or outer member to which the eyelet corresponds. Thus, relative motion between the pedicle screw and eyelet is possible, permitting a wide range of motion and a variety of orientations that may be required when assembling the facet joint, as well as when the facet joint is in the assembled state.

FIG. 6 is an illustration a perspective view of an offset eyelet in accordance with the present disclosure. The offset eyelet has an alternate configuration than the eyelet of FIG. 5, and generally has cylindrical shape with a centrally located opening to accommodate a pedicle screw, or anchoring feature. The offset eyelet is generally cylindrical in shape and has an outer diameter. The offset eyelet has an upper surface and a lower surface. The upper surface and lower surface of the offset eyelet are approximately planar and a corresponding upper surface of an offset eyelet of an adjacent inner or outer member will be in contact when assembled (see FIG. 7), in an overlapping fashion with centrally located openings aligned. The offset eyelet is either stepped up or down from the shaft to which the offset eyelet is attached and a rim is formed where the step occurs. Thus, when assembled, the upper surfaces of the offset eyelet of an adjacent component will have the offset eyelet as configured in FIG. 6, would be in contact and the step between shaft and eyelet will permit shafts of adjacent members to be approximately aligned in plane with the outer diameter of the offset eyelet being constrained by the rim of the adjacent member. Even though the shafts of adjacent members are aligned in plane, the shafts themselves are able to move angularly relative to each other, with a single pedicle screw arranged through the centrally located openings of the overlapping offset eyelets establishing a "pivot point." Relative motion between the pedicle screw and offset eyelet is possible, permitting a wide range of motion and a variety of orientations that may be required when assembling the facet joint, as well as when the facet joint is in the assembled state.

Figure 7:
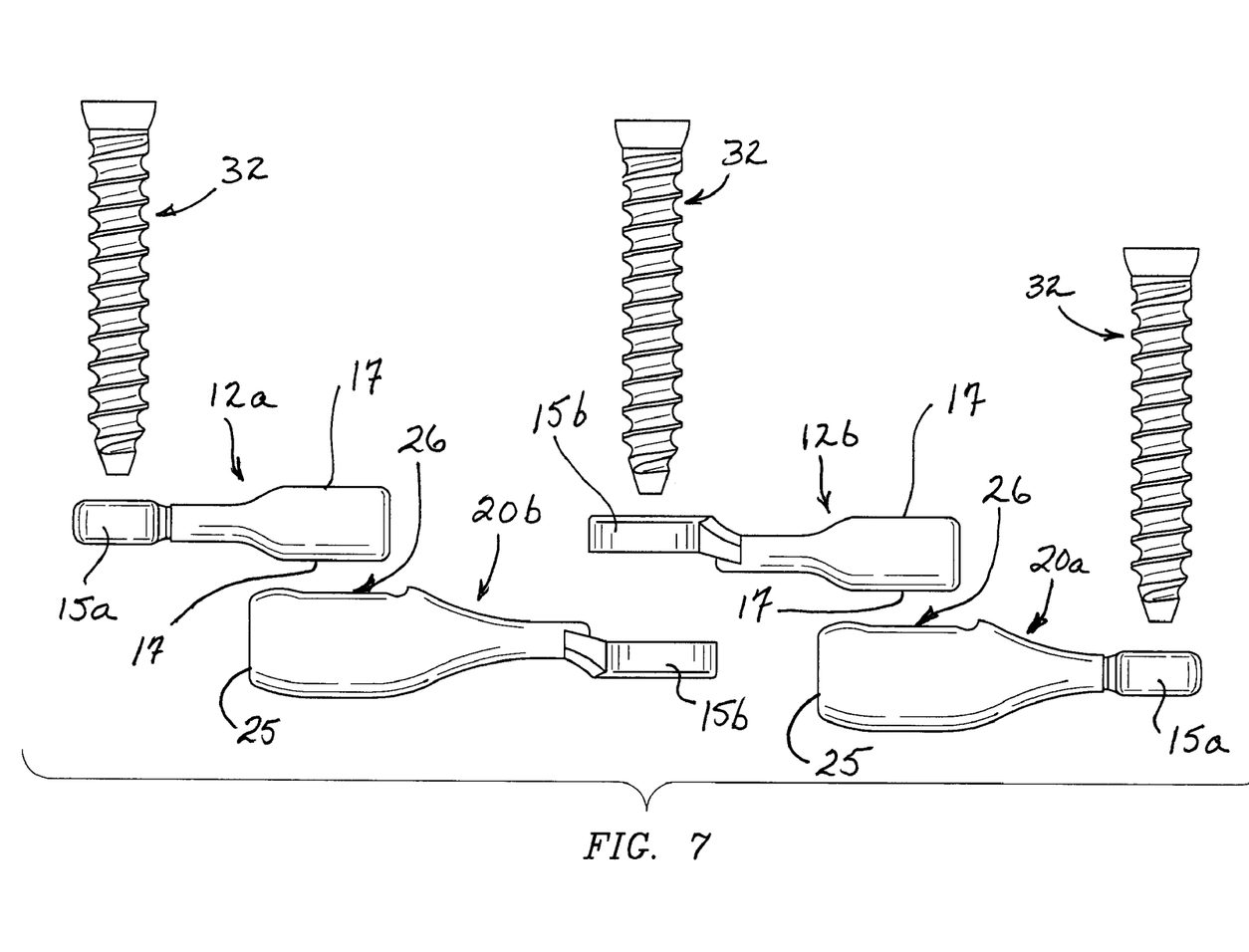
FIG. 7 is an illustration of an exploded side view of one embodiment of a facet joint prosthesis in accordance with the present disclosure.

Turning now to FIG. 7, an exploded side view of a facet joint assembly is illustrated. The facet joint assembly comprises two inner members, two outer members, and three pedicle screws and is a configuration capable of spanning three adjacent vertebrae with one pedicle screw being anchored into a vertebrae. Alternate configurations are achievable, with two vertebrae being the minimum span. If only two vertebrae are to be spanned, then the inner and outer member would comprise eyelet configurations as discussed in connection with FIG. 5.

With reference to FIGS. 1 to 7, and in the context of installation within an intervertebral space of a spinal column, the assembly of the facet joint will be discussed. There are numerous acceptable methods for installing the facet joint prosthesis, as those skilled in the art will recognize; although only one of such methods is discussed in connection with this disclosure, others will be recognized.

One method of installing a facet joint to span a single intervertebral space may be as follows. During surgery, two holes are drilled on one side of the vertebral column for pedicle screws to be inserted. The facet joint prosthesis is adjustable between a disassembled state, in which pedicle screws and inner and outer members are not secured to one another, and the assembled state. In an assembled state, a first pedicle screw is inserted through the central opening of the eyelet an inner member as to allow articulation of the inner member and the first pedicle screw. However, assembly of the facet joint is equally feasible if one begins the assembly process installing an outer member initially. The first pedicle screw is installed within the vertebrae but not tightened into a final position, which is the position the pedicle screw will remain during normal use. In this position, the pedicle screw is secure in the vertebrae and the inner to member is free to articulate about the screw. An outer member is now linked to the inner member by aligning the slot on the outer member with the faceted surface, or faceted surfaces, of the bulbous portion of the inner member thus enabling the bulbous portion of the inner member to be inserted into the cavity of the outer member. With the bulbous portion of the inner member arranged within the cavity of the outer member, the outer member is rotated, either clockwise or counterclockwise, until the inner member and outer member are secured together, forming a link, or facet joint. Thus, the link is capable of articulating in a rotational fashion, a linear fashion, and combinations of linear and translational articulations. This is necessary to properly orient the facet joint in a final orientation. With the facet joint articulated to the final orientation, a second pedicle screw is inserted through the central opening of the offset eyelet of the outer member, and installed in the hole in the drilled vertebrae adjacent the intervertebral space. The pedicle screws are tightened to their final position facet joint is properly installed. As indicated above, this is but one method of installing the facet joint and variations of the installation process may be possible, with the above identified steps being performed in a different sequence.

Multiple intervertebral spaces may also be spanned with the facet joint as disclosed with the installation being similar to that described above. For example, the facet prosthesis may be installed to span two adjacent intervertebral spaces. During surgery, holes are drilled on one side of the vertebral column for the pedicle screws to be inserted. Holes are placed only in vertebrae which bound the intervertebral space. A first pedicle screw is inserted through the central opening of the eyelet of a first inner member as to allow articulation between the first inner member and the first pedicle screw. The first pedicle screw is inserted into the drilled hole in a first vertebrae, but not tightened into its final position. A first outer member is now linked to the first inner member in the manner as discussed above. A second pedicle screw is inserted through the central opening of the eyelet of a second outer member and inserted into the drilled hole in a second vertebrae, but not tightened into its final position thus permitting articulation between the second outer member and the second pedicle screw. A second inner member is now linked to the second outer member in the manner as discussed above. The offset eyelet of the first outer member and the offset eyelet of the second inner member are now aligned so a third pedicle screw can be inserted through the aligned central openings of the aligned offset eyelets. Thus, a facet joint having multiple links is capable of articulating in a rotational fashion, a linear fashion, and combinations of linear and translational articulations. The facet joint articulated to the final orientation and the third pedicle screw is inserted and installed in the hole in a third vertebrae, the third vertebrae being between and adjacent the first and second vertebrae. The pedicle screws are tightened to their final position facet joint is properly installed. This process may be repeated, as necessary, depending on the number of intervertabral spaces to be spanned.

When the facet joint prosthesis is in the assembled state, there is no requirement that the pedicle screws be at the same vertical position relative to one another, or, for that matter, be oriented such that their longitudinal axes are perfectly parallel to one another. This is made possible by the free play afforded the facet joint by virtue of the articulation of the inner and outer members when assembled and forming a link having a wide range of motion. It is understood that, like the other embodiments described herein, one may assemble the components in a different order, yet arrive at the same final assembly.

As mentioned above, inner and outer members come in different lengths. During surgery, inner and outer members of differing lengths are made available, an inner or outer member of an appropriate length perhaps being selected during the surgery itself. It is further understood that the various components are packaged, sold or otherwise made available as kits since they are to be used together. Thus, a first kit may comprise a pedicle screw and an inner or outer member; a second kit may comprise a pedicle screw, an inner member and an outer member; a third kit may comprise two pedicle screws, and an inner and an outer member; a fifth kit may comprise all the items of the fourth kit plus a plurality of inner and outer members of different lengths, and so forth.

It will be apparent to those skilled in the art that various modifications and variations can be made without departing from the spirit or scope of the invention

What is claimed is:

1. A facet joint prosthesis comprising:
 a first pedicle screw, a second pedicle screw and a third pedicle screw, wherein the first pedicle screw, second pedicle screw and third pedicle screw each comprise a threaded shaft and a screw head;
 first outer member comprising a first end and a second end, wherein the first end comprises an open ended elongate bulbous portion, the open ended elongate bulbous portion having an open end and an elongate bulbous cavity central to the elongate bulbous portion, the elongate bulbous portion tapering to a shaft via a neck portion, the shaft extending toward the second end, wherein the second end comprises an eyelet having a central passage that receives the first pedicle screw and a beveled inner rim that surrounds the central passage and supports the first pedicle screw head; and
 first inner member comprising a first end and a second end, wherein the first end comprises an elongate bulbous portion that tapers to a shaft via a neck portion, the shaft extending toward the second end, wherein the second end comprises an eyelet having a central passage that receives the second pedicle screw and a beveled inner rim that surrounds the central passage and supports the second pedicle screw head;
 a second outer member comprising a first end and a second end, wherein the first end comprises an open ended elongate bulbous portion, the open ended elongate bulbous portion having an open end and an elongate bulbous cavity central to the elongate bulbous portion, the elongate bulbous portion tapering to a shaft via a neck portion, the shaft extending toward the second end, wherein the second end comprises an offset eyelet having a central passage that receives the third pedicle screw, the offset eyelet being either stepped up or stepped down from the shaft to which the offset eyelet is attached; and a second inner member comprising a first end and a second end, wherein the first end comprises an elongate bulbous portion that tapers to a shaft via a neck portion, the shaft extending toward the second end, wherein the second end comprises an offset eyelet having a central passage that receives the third pedicle screw, the offset eyelet being either stepped up or stepped down from the shaft to which the offset eyelet is attached, wherein the elongate bulbous cavity of the first outer member receives the elongate bulbous portion of the second inner member through a cavity slot in the open ended elongate bulbous portion of the first outer member, with the shaft of the second inner member extending out of the open end of the open ended elongate bulbous portion of the first outer member, wherein the elongate bulbous cavity of the second outer member receives the elongate bulbous portion of the first inner member through a cavity slot in the open ended elongate bulbous portion of the second outer member, with the shaft of the first inner member extending out of the open end of the open ended elongate bulbous portion of the second outer member, and wherein the offset eyelet of the second outer member and the offset eyelet of the second inner member are so constructed as to align with one another in a manner that the shafts of the second outer member and the second inner member will be approximately aligned in plane when the third pedicle screw is received through the two, respective, offset eyelets.

2. A facet joint prosthesis comprising:

a first pedicle screw, a second pedicle screw and a third pedicle screw, wherein the first pedicle screw, second pedicle screw and third pedicle screw each comprise a threaded shaft and a screw head;

a first outer member comprising a first end and a second end, wherein the first end comprises
 an open ended elongate bulbous portion,
 the open ended elongate bulbous portion having an open end, a cavity central to the elongate bulbous portion, and a longitudinally extending cavity slot formed in the elongate bulbous portion extending through and from the open end of the elongate bulbous portion longitudinally toward the second end of the first outer member and defining an access to the cavity, the cavity slot exhibiting a defined size and shape,
 the elongate bulbous portion tapering to a shaft via a neck portion, the shaft extending toward the second end,
 wherein the second end of the first outer member comprises an attachment feature that receives the first pedicle screw;

second outer member comprising a first end and a second end, wherein the first end comprises
 an open ended elongate bulbous portion,
 the open ended elongate bulbous portion having an open end, a cavity central to
 the elongate bulbous portion, and a longitudinally extending cavity slot formed in the elongate bulbous portion extending through and from the open end of the elongate bulbous portion longitudinally toward the second end of the second outer member and defining an access to the cavity, the cavity slot exhibiting a defined size and shape,
 the elongate bulbous portion tapering to a shaft via a neck portion, the shaft extending toward the second end,
 wherein the second end of the second outer member comprises an attachment feature that receives the third pedicle screw;

first inner member comprising a first end and a second end, wherein the first end comprises
 an elongate portion that transitions to a shaft, the shaft extending toward the second end,
 the elongate portion being of a size and shape that will cooperate with the defined size and shape of the cavity slot of the second outer member to allow entry of the elongate portion of the first inner member into the cavity of the second outer member through the cavity slot yet not its removal through the open end of the second outer member, and
 wherein the second end of the first inner member comprises an attachment feature that receives the second pedicle screw;

second inner member comprising a first end and a second end, wherein the first end comprises
 an elongate portion that transitions to a shaft, the shaft extending toward the second end,
 the elongate portion being of a size and shape that will cooperate with the defined size and shape of the cavity slot of the first outer member to allow entry of the elongate portion of the second inner member into the cavity of the second outer member through the cavity slot yet not its removal through the open end of the second outer member, and
 wherein the second end comprises an attachment feature that receives the third pedicle screw, wherein the attachment feature of the second outer member and the attachment feature of the second inner member are so constructed as to cooperate with one another in a manner that the shafts of the second outer member and the second inner member will be approximately aligned in plane when the third pedicle screw is received through the two, respective, attachment features.

3. The facet joint prosthesis of claim 2, wherein the elongate portion of each of the first inner member and second inner member is an elongate bulbous portion and wherein the elongate bulbous portion is defined with multiple facets arranged on its periphery, such facets being positioned and sized to cooperate with the size and shape of the cavity slot of the respective second outer member and first outer member to permit passage of the elongate bulbous portion of the respective inner member though the respective cavity slot when the bulbous portion is in a first orientation relative to the slot, but not permit passage of the elongate bulbous portion of the respective inner member though the respective cavity slot when the bulbous portion in a second orientation relative to the slot.

4. The facet joint prosthesis of claim 2, wherein the attachment feature the first inner member has a beveled inner rim that surrounds a central passage and supports the second pedicle screw head and the attachment feature of the first outer member has a beveled inner rim that surrounds a central passage and supports the first pedicle screw head.

5. The facet joint prosthesis of claim 2, wherein
 the attachment feature of the second inner member comprises an offset eyelet having a central passage that receives the third pedicle screw, the offset eyelet being either stepped up or stepped down from the shaft to which the offset eyelet is attached, the attachment feature of the second outer member comprises an offset eyelet having a central passage that receives the third pedicle screw, the offset eyelet being either stepped up or stepped down from the shaft to which the offset eyelet is attached, and
the offset eyelet of the second outer member and the offset eyelet of the second inner member are so constructed as to align with one another in a manner that the shafts of the second outer member and the second inner member will be approximately aligned in plane when the third pedicle screw is received through the two, respective, offset eyelets.

6. The facet joint prosthesis of claim 4, wherein
the attachment feature of the second inner member comprises an offset eyelet having a central passage that receives the third pedicle screw, the offset eyelet being either stepped up or stepped down from the shaft to which the offset eyelet is attached,
the attachment feature of the second outer member comprises an offset eyelet having a central passage that receives the third pedicle screw, the offset eyelet being either stepped up or stepped down from the shaft to which the offset eyelet is attached, and
the offset eyelet of the second outer member and the offset eyelet of the second inner member are so constructed as to align with one another in a manner that the shafts of the second outer member and the second inner member will be approximately aligned in plane when the third pedicle screw is received through the two, respective, offset eyelets.

\* \* \* \* \*